United States Patent
Addison et al.

(10) Patent No.: US 8,870,783 B2
(45) Date of Patent: Oct. 28, 2014

(54) PULSE RATE DETERMINATION USING GAUSSIAN KERNEL SMOOTHING OF MULTIPLE INTER-FIDUCIAL PULSE PERIODS

(75) Inventors: Paul S. Addison, Midlothian (GB); James Watson, Fife (GB)

(73) Assignee: Covidien LP, Mansfield, MA (US)

( * ) Notice: Subject to any disclaimer, the term of this patent is extended or adjusted under 35 U.S.C. 154(b) by 247 days.

(21) Appl. No.: 13/307,453

(22) Filed: Nov. 30, 2011

(65) Prior Publication Data

US 2013/0137945 A1 May 30, 2013

(51) Int. Cl.
*A61B 5/02* (2006.01)

(52) U.S. Cl.
USPC .......................................................... 600/500

(58) Field of Classification Search
USPC .................................. 600/500–507, 322–326
See application file for complete search history.

(56) References Cited

U.S. PATENT DOCUMENTS

| | | | |
|---|---|---|---|
| 4,289,141 A | 9/1981 | Cormier | |
| 4,510,944 A * | 4/1985 | Porges | 600/500 |
| 5,299,570 A | 4/1994 | Hatschek | |
| 5,402,778 A | 4/1995 | Chance | |
| 5,416,582 A | 5/1995 | Knutson et al. | |
| 5,439,483 A | 8/1995 | Duong-Van | |
| 5,562,596 A * | 10/1996 | Pincus et al. | 600/17 |
| 5,626,140 A | 5/1997 | Feldman et al. | |
| 5,682,898 A * | 11/1997 | Aung et al. | 600/484 |
| 5,778,881 A | 7/1998 | Sun et al. | |
| 5,795,304 A | 8/1998 | Sun et al. | |
| 5,797,840 A | 8/1998 | Akselrod et al. | |
| 5,818,583 A | 10/1998 | Sevick-Muraca et al. | |
| 5,827,195 A | 10/1998 | Lander | |
| 5,938,594 A | 8/1999 | Poon et al. | |
| 6,070,098 A | 5/2000 | Moore-Ede et al. | |
| 6,135,966 A | 10/2000 | Ko | |
| 6,208,951 B1 | 3/2001 | Kumar et al. | |
| 6,245,022 B1 * | 6/2001 | Archibald et al. | 600/485 |
| 6,339,715 B1 * | 1/2002 | Bahr et al. | 600/323 |
| 6,397,096 B1 | 5/2002 | Liu et al. | |
| 6,411,839 B1 * | 6/2002 | Okinishi | 600/479 |
| 6,463,311 B1 * | 10/2002 | Diab | 600/324 |
| 6,505,060 B1 * | 1/2003 | Norris | 600/323 |
| 6,549,284 B1 | 4/2003 | Boas et al. | |
| 6,614,226 B2 * | 9/2003 | Wedeen | 324/309 |
| 6,647,280 B2 * | 11/2003 | Bahr et al. | 600/323 |
| 6,658,277 B2 | 12/2003 | Wasserman | |

(Continued)

FOREIGN PATENT DOCUMENTS

WO    WO 9608992 A2    3/1996
WO    WO 0140776 A1    6/2001

(Continued)

*Primary Examiner* — Jacqueline Cheng
*Assistant Examiner* — Corey B Hipps
(74) *Attorney, Agent, or Firm* — Fletcher Yoder PC (57) ABSTRACT

Systems and methods are provided for determining the pulse rate of a patient from multiple fiducial points using Gaussian kernel smoothing. Based on acquired pleth signals, each recorded fiducial pulse period is converted to a Gaussian kernel function. The Gaussian kernel functions for all recorded fiducial points are summed to generate a Gaussian kernel smoothed curve. The pulse rate of a patient may be determined from the Gaussian kernel smoothed curve. All acquired fiducial pulse periods contribute to generate the Gaussian kernel smoothing curve. The number of fiducial points utilized may change to improve pulse rate determination or provide additional functionality to the system.

18 Claims, 7 Drawing Sheets

(56) References Cited

U.S. PATENT DOCUMENTS

| | | |
|---|---|---|
| 6,701,170 B2 | 3/2004 | Stetson |
| 6,816,741 B2 * | 11/2004 | Diab ............................ 600/324 |
| 6,944,322 B2 | 9/2005 | Johnson et al. |
| 6,988,056 B2 | 1/2006 | Cook |
| 7,004,907 B2 | 2/2006 | Banet et al. |
| 7,027,850 B2 | 4/2006 | Wasserman |
| 7,031,857 B2 | 4/2006 | Tarassenko et al. |
| 7,044,918 B2 * | 5/2006 | Diab ............................ 600/502 |
| 7,054,453 B2 | 5/2006 | Causevic et al. |
| 7,054,454 B2 | 5/2006 | Causevic et al. |
| 7,060,035 B2 | 6/2006 | Wasserman |
| 7,062,307 B2 | 6/2006 | Norris et al. |
| 7,079,880 B2 | 7/2006 | Stetson |
| 7,079,888 B2 | 7/2006 | Oung et al. |
| 7,187,441 B1 | 3/2007 | Sevick-Muraca et al. |
| 7,190,994 B2 * | 3/2007 | Mohler et al. ............... 600/514 |
| 7,190,995 B2 | 3/2007 | Chervin et al. |
| 7,215,991 B2 | 5/2007 | Besson et al. |
| 7,225,013 B2 | 5/2007 | Geva et al. |
| 7,251,518 B2 | 7/2007 | Herrmann |
| 7,254,500 B2 | 8/2007 | Makeig et al. |
| 7,268,873 B2 | 9/2007 | Sevick-Muraca et al. |
| 7,336,982 B2 | 2/2008 | Yoo |
| 7,343,187 B2 | 3/2008 | Stetson |
| 7,375,347 B2 | 5/2008 | Colvin, Jr. et al. |
| 7,407,485 B2 | 8/2008 | Huiku |
| 7,519,488 B2 | 4/2009 | Fu et al. |
| 7,641,614 B2 * | 1/2010 | Asada et al. ................. 600/485 |
| 8,430,817 B1 * | 4/2013 | Al-Ali et al. ................. 600/301 |
| 8,494,829 B2 * | 7/2013 | Teixeira ............................ 703/11 |
| 2002/0137995 A1 * | 9/2002 | Heckel ........................ 600/323 |
| 2003/0114767 A1 * | 6/2003 | Heim ............................. 600/504 |
| 2003/0229289 A1 * | 12/2003 | Mohler et al. ............... 600/508 |
| 2004/0010188 A1 | 1/2004 | Wasserman |
| 2004/0059210 A1 | 3/2004 | Stetson |
| 2004/0087846 A1 | 5/2004 | Wasserman |
| 2005/0175540 A1 | 8/2005 | Oraevsky et al. |
| 2005/0197579 A1 | 9/2005 | Baker, Jr. |
| 2005/0228301 A1 | 10/2005 | Banet et al. |
| 2006/0058595 A1 | 3/2006 | Herrmann |
| 2006/0074333 A1 | 4/2006 | Huiku |
| 2006/0084878 A1 | 4/2006 | Banet et al. |
| 2006/0111644 A1 * | 5/2006 | Guttag et al. ................. 600/544 |
| 2006/0206021 A1 * | 9/2006 | Diab ............................ 600/336 |
| 2006/0217614 A1 | 9/2006 | Takala et al. |
| 2006/0217615 A1 | 9/2006 | Huiku et al. |
| 2006/0217628 A1 | 9/2006 | Huiku |
| 2006/0229519 A1 | 10/2006 | Fujiwara et al. |
| 2006/0253067 A1 * | 11/2006 | Staib et al. ..................... 604/67 |
| 2006/0258921 A1 | 11/2006 | Addison et al. |
| 2007/0010723 A1 | 1/2007 | Uutela et al. |
| 2007/0049845 A1 * | 3/2007 | Fleischman et al. ......... 600/561 |
| 2007/0055163 A1 | 3/2007 | Asada et al. |
| 2007/0208235 A1 | 9/2007 | Besson et al. |
| 2007/0213619 A1 | 9/2007 | Linder |
| 2007/0276269 A1 * | 11/2007 | Yun et al. ..................... 600/504 |
| 2008/0045832 A1 | 2/2008 | McGrath |
| 2008/0064965 A1 * | 3/2008 | Jay et al. ..................... 600/484 |
| 2008/0076986 A1 | 3/2008 | Pav |
| 2008/0077022 A1 | 3/2008 | Baker |
| 2008/0077029 A1 * | 3/2008 | Mohler et al. ............... 600/509 |
| 2008/0081974 A1 | 4/2008 | Pav |
| 2008/0082018 A1 | 4/2008 | Sackner et al. |
| 2008/0137066 A1 | 6/2008 | Weinstein et al. |
| 2008/0146895 A1 | 6/2008 | Olson et al. |
| 2008/0269583 A1 | 10/2008 | Reisfeld |
| 2008/0275349 A1 | 11/2008 | Halperin et al. |
| 2009/0149815 A1 * | 6/2009 | Heim ............................. 600/504 |
| 2009/0326353 A1 * | 12/2009 | Watson et al. ................ 600/330 |
| 2010/0016676 A1 * | 1/2010 | Addison et al. .............. 600/300 |
| 2010/0099993 A1 * | 4/2010 | Cohen et al. ................. 600/485 |
| 2010/0137727 A1 * | 6/2010 | Sameni et al. ............... 600/511 |
| 2010/0268096 A1 * | 10/2010 | Berka et al. .................. 600/485 |
| 2010/0298728 A1 * | 11/2010 | Addison et al. .............. 600/504 |
| 2012/0022350 A1 * | 1/2012 | Teixeira ........................ 600/324 |
| 2012/0203122 A1 * | 8/2012 | Kinrot et al. ................. 600/506 |
| 2012/0203166 A1 * | 8/2012 | Riback et al. .................. 604/66 |
| 2013/0024123 A1 * | 1/2013 | Ochs et al. ..................... 702/19 |

FOREIGN PATENT DOCUMENTS

| | | |
|---|---|---|
| WO | WO 2004075746 | 9/2004 |
| WO | WO 2006100685 A2 | 9/2006 |
| WO | WO 2007131064 A2 | 11/2007 |
| WO | WO 2007131066 A2 | 11/2007 |

\* cited by examiner

PULSE RATE DETERMINATION USING GAUSSIAN KERNEL SMOOTHING OF MULTIPLE INTER-FIDUCIAL PULSE PERIODS

BACKGROUND

The present disclosure relates generally to medical devices and, more particularly, to sensors used for techniques for determining physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of healthcare, caregivers (e.g., doctors and other healthcare professionals) often desire to monitor certain physiological characteristics of their patients. Accordingly, a wide variety of monitoring devices have been developed for monitoring many such physiological characteristics. These monitoring devices often provide doctors and other healthcare personnel with information that facilitates provision of the best possible healthcare for their patients. As a result, such monitoring devices have become an indispensable part of modern medicine.

One technique for monitoring physiological characteristics of a patient is commonly referred to as pulse oximetry, and the devices built based upon pulse oximetry techniques are commonly referred to as pulse oximeters. Pulse oximeters may be used to measure and monitor various blood flow characteristics of a patient. For example, a pulse oximeter may be utilized to monitor the blood oxygen saturation of hemoglobin in arterial blood, the volume of individual blood pulsations supplying the tissue, and/or the rate of blood pulsations corresponding to each heartbeat of a patient. In fact, the "pulse" in pulse oximetry refers to the time varying amount of arterial blood in the tissue during each cardiac cycle.

Pulse oximeters typically utilize a non-invasive sensor that transmits light through a patient's tissue and that photoelectrically detects the absorption and/or scattering of the transmitted light in such tissue. One or more of the above physiological characteristics may then be calculated based upon the amount of light absorbed or scattered using various algorithms.

In practice, a pulse oximeter may be employed to provide a running assessment of a patient's physiological signs, such as pulse rate and blood oxygen saturation, and to indicate when one or more of the monitored characteristics crosses an alarm or threshold value. However, pulse rate measurements usually require initialization time to acquire the data needed before an accurate measurement of the patient's heartbeat is determined. Also, the quality of the signal is not always consistent, leading to possible variations in the data and inaccurate measurements.

BRIEF DESCRIPTION OF THE DRAWINGS

Advantages of the disclosed systems and techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Present embodiments relate to systems and methods for determining the pulse rate of a patient from inter-fiducial pulse periods using Gaussian kernel smoothing. In one embodiment, one or more fiducial points are selected on a received plethysmographic (pleth) signal, such as a pulse oximeter signal. Fiducial pulse periods are determined and converted into Gaussian kernel functions. These Gaussian kernel functions are subsequently summed to create a smooth distribution from which the pulse rate is derived as the peak of the smoothed distribution. The pulse rate determination derived by this method may incorporate all recorded pulse periods. In some embodiments, the selected number and identity of fiducial points may vary during operation.

The received pleth signal may be filtered. After the signal is filtered, fiducial points are selected to determine fiducial pulse periods. In some embodiments, the pulse periods are filtered to remove outliers, for example those that do not correspond to the physiological conditions of the patient. The fiducial pulse periods are then converted into Gaussian kernel functions and summed to create a smoothed distribution. The pulse rate is derived from the peak of the smoothed distribution.

In a certain embodiment, the fiducial points are selected based on a ranking. The ranking may relate to the reliability, consistency, location, and/or quality of each fiducial point. The pulse periods determined from these ranked fiducial points are then converted into Gaussian kernel functions and summed to create a smoothed distribution. The pulse rate is derived from the peak of the smoothed distribution. Based on this distribution and/or user input and settings, the number of ranked fiducial points utilized may change. The number of fiducial points may be changed to increase the accuracy of a pulse rate, gain additional physiological information, counter noise, counter the effects of irregular fiducial points, and/or conserve energy. The fiducial ranking may be static or dynamic. With a dynamic fiducial ranking, the rank of fiducial points may be changed based on factors (e.g., reliability) relating to the data obtained from the fiducial points. In some embodiments, only highly ranked points are utilized, thus lowering the ranking of a fiducial point may cause that fiducial point to not be utilized.

Figure 1:
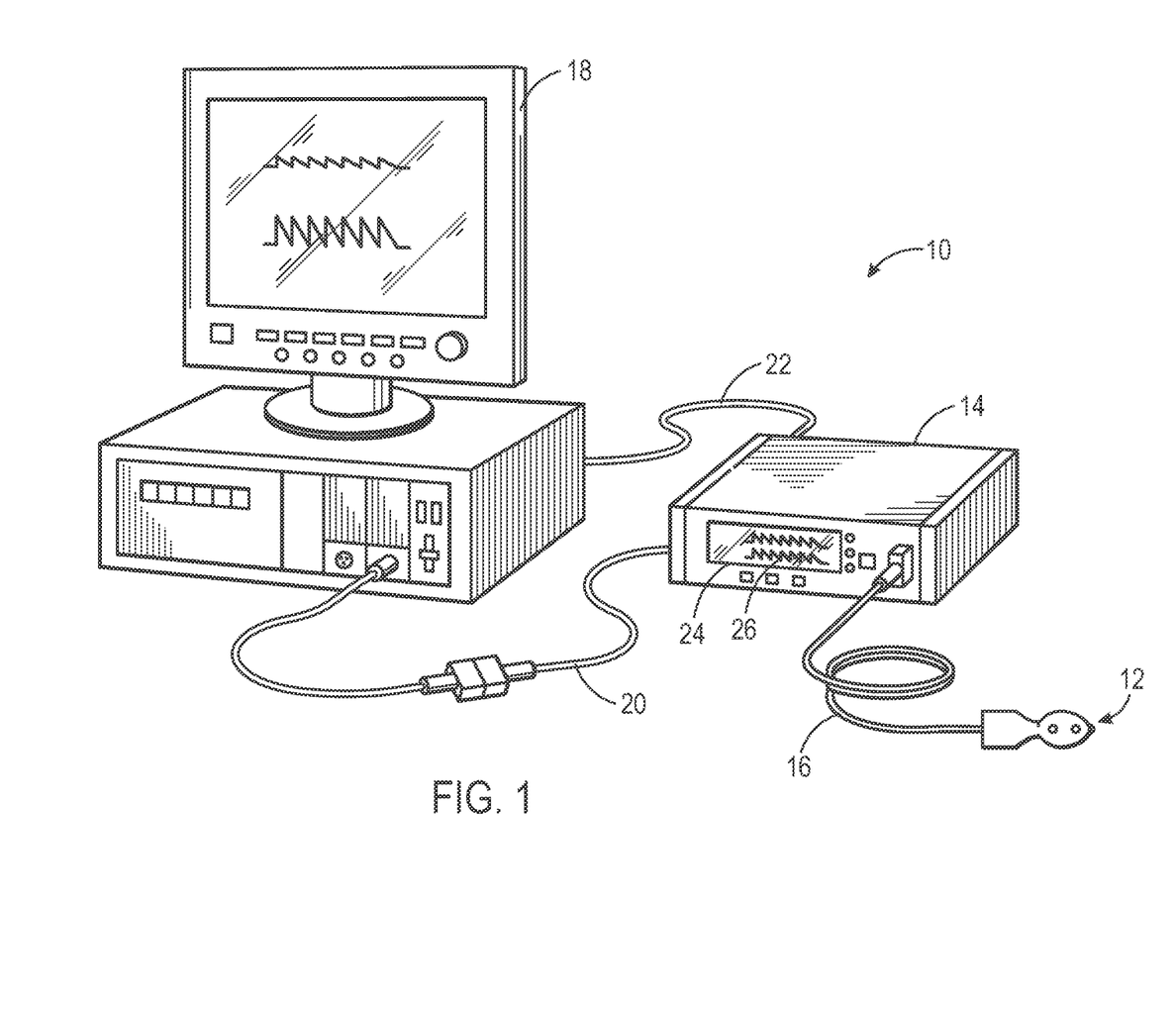
FIG. 1 depicts a diagram of an embodiment of a spectrophotometric system.

Turning to FIG. 1, a perspective view depicts a spectrophotometric system 10. The sensor 12 may be coupled to the monitor 14 via sensor cable 16. The spectrophotometric system 10 may be any suitable pulse oximeter or hemometer such as those that may be available from Nellcor Puritan Bennett LLC. Furthermore, to upgrade conventional operation provided by the monitor 14 to provide additional functions, the monitor 14 may be coupled to a multi-parameter patient monitor 18 via a cable 20 connected to a sensor input port or via a cable 22 connected to a digital communication port, for example.

The monitor 14 may display calculated parameters on a display 24. As illustrated in FIG. 1, the display 24 may be integrated into the monitor 14. The display 24 may display computed physiological data including, for example, an oxygen saturation percentage, a pulse rate, and/or a plethysmographic waveform 26.

The sensor 12 may be of a disposable or a non-disposable type. Furthermore, the sensor 12 may obtain readings from a patient 28 (FIG. 2), which can be used by the monitor 14 to calculate certain physiological characteristics such as the blood-oxygen saturation of hemoglobin in arterial blood, the volume of individual blood pulsations supplying the tissue, and/or the rate of blood pulsations corresponding to each heartbeat of a patient 28.

Figure 2:
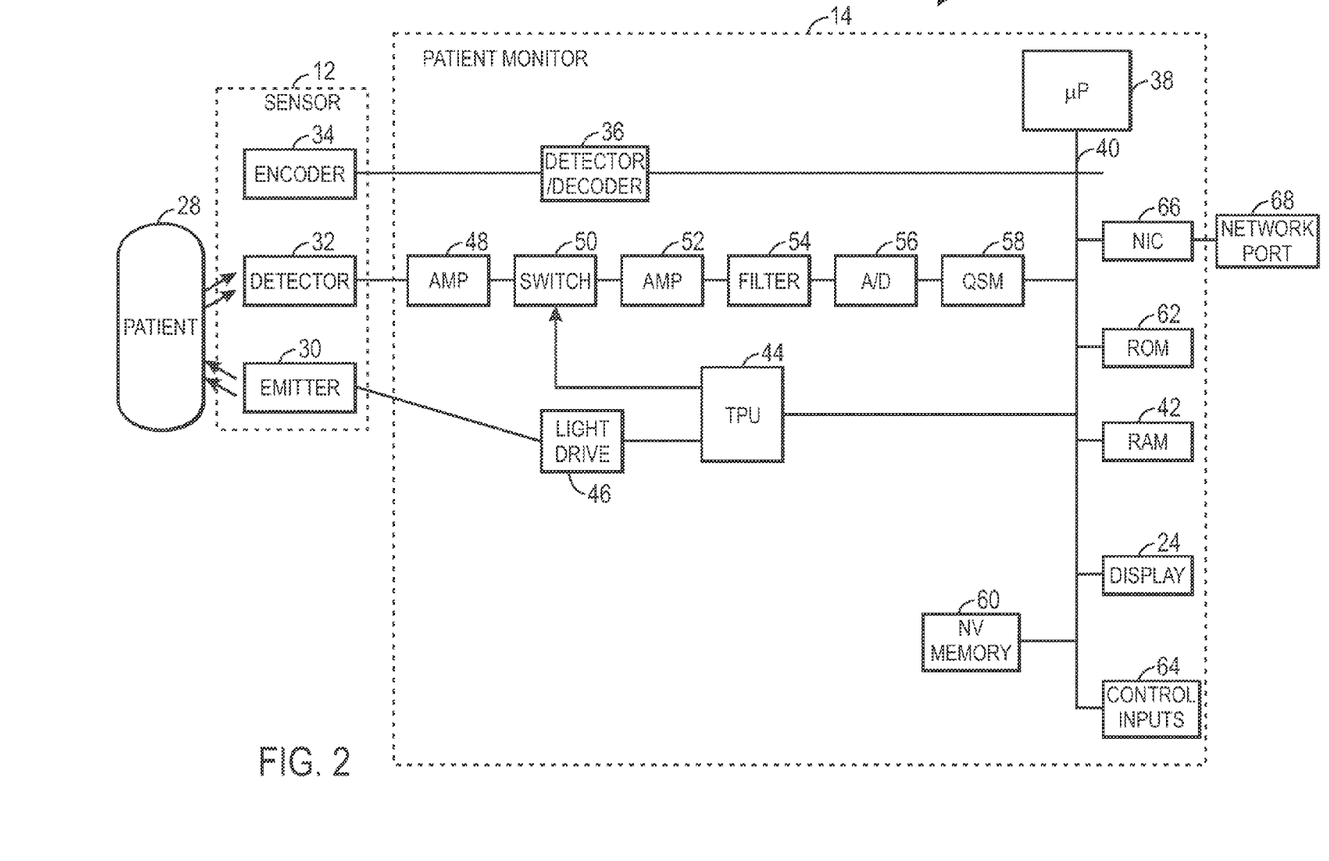
FIG. 2 is a block diagram of an embodiment of a spectrophotometric system.

Turning to FIG. 2, a simplified block diagram of a spectrophotometric system 10 is illustrated in accordance with an embodiment. The sensor 12 may contain a light source, i.e. an emitter 30, a detector 32, and an encoder 34. The emitter 30 may have one or more light sources that transmit electromagnetic radiation, i.e., light, into the tissue of a patient 28. For example, the emitter 30 may include a plurality of LEDs operating at discrete wavelengths, such as in the red and infrared portions of the electromagnetic radiation spectrum. Alternatively, the emitter 30 may be a broad spectrum emitter, or it may include wavelengths for measuring water fractions, hematocrit, or other physiologic parameters. Light may be transmitted from the emitter 30, and may pass into a blood perfused tissue of a patient 28 whereby it may be scattered and/or absorbed, and then detected by the detector 32. The detector 32 may be a photoelectric detector which may detect the scattered and/or absorbed light from the patient 28. Based on the detected light, the detector 32 may generate an electrical signal, e.g., current, at a level corresponding to the detected light. The sensor 12 may direct the electrical signal to the monitor 14 for processing and calculation of physiological parameters. The electrical signal may include repeated patterns, or waves. The electrical signal may also include non-physiological signal components resulting from noise sources such as sensor type, incorrect sensor placement, and/or movement of the patient 28. The non-physiological signal components in the pleth signal may decrease the reliability of the signal as noise may decrease the accuracy of certain physiological data, including pulse rate.

Additionally, the sensor 12 may include an encoder 34, which may be capable of providing signals relating to the properties of the emitter 30 to allow the spectrophotometric system 10 to process the electrical signal from the sensor as desired to calculate oxygen saturation of the patient or other physiological characteristics of the patient 28 such as pulse rate. The encoder 34 may be a memory device, such as an erasable programmable read only memory (EPROM), that stores information. The encoder 34 may be communicatively coupled to the monitor 14 in order to communicate information to the decoder 36. The decoder 36 may receive and decode the information from the encoder 34. Once decoded, the information may be transmitted to the processor 38 for utilization in calculation of the physiological parameters of the patient 28.

Accordingly, the sensor 12 may be connected to a pulse oximetry monitor 14. The monitor 14 may include a microprocessor 38 coupled to an internal bus 40. Also connected to the bus 40 may be a RAM memory 42, ROM memory 62, network interface card 66, a display 24, and a time processing unit (TPU) 44. A TPU 44 may provide timing control signals to light drive circuitry 46, which controls when the emitter 30 is activated, and if multiple light sources are used, the multiplexed timing for the different light sources. TPU 44 may also control the gating-in of signals from detector 32 through an amplifier 48 and a switching circuit 50. These signals are sampled at the proper time, depending at least in part upon which of multiple light sources is activated, if multiple light sources are used. The received signal from the detector 32 may be passed through an amplifier 52, a low pass filter 54, and an analog-to-digital converter 56 for amplifying, filtering, and digitizing the electrical signals the from the sensor 12. The digital data may then be stored in a queued serial module (QSM) 58, for later downloading to RAM 42 as QSM 58 fills up.

Nonvolatile memory 60 may store caregiver preferences, patient information, or various parameters such as ranked fiducial points discussed below, which may be used to determine pulse rate by Gaussian kernel smoothing. Software for performing the configuration of the monitor 14 and for carrying out the techniques described herein may also be stored on the nonvolatile memory 60, or may be stored on the ROM 62. The visual notifications of the operational status of the sensor 12, as well as other notifications may be shown by display 24 and manipulated through control inputs 64. A NIC 66 may be connected to a network port 68 and be used to deliver, for example, the operational status of the sensor 12, any alerts or notifications, physiologic measurements, or instructions relating to the number of fiducial points utilized. The network may be a wired or wireless network, such as a Wi-Fi network.

Figure 3:
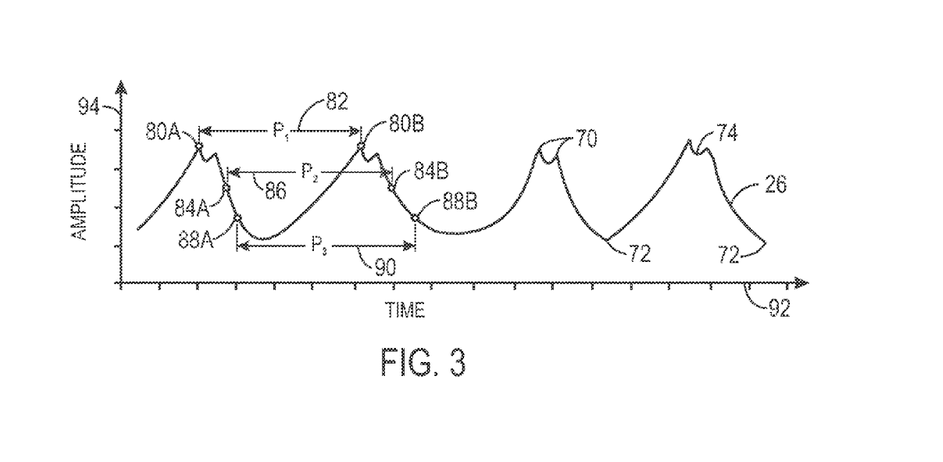
FIG. 3 is a chart depicting a hypothetical plethysmographic signal with fiducial points and pulse periods indicated, in accordance with aspects of the present disclosure.

Turning to FIG. 3, an example of a pleth waveform signal 26 is shown to illustrate the present technique. A pleth signal 26 as illustrated in FIG. 3 corresponds with the heart pulsations of a patient, resulting in a signal relating to light intensity indicative of volume changes 94 over time 92. Features of the pleth signal 26 relate to specific physiological events such as systolic and diastolic phases of the cardiac cycle. A pleth signal 26 has peaks 70, troughs 72, and a dicrotic notch 74, among other distinguishing characteristics. Points along the pleth signal 26 with characteristics that only come about once every wave may be called fiducial points. Fiducial points are useful to accurately calculate pulse rate since the period of the pleth signal 26 can be determined from the distance between corresponding fiducial points on consecutive waves of the pleth signal 26. Fiducial points may be located from the original pleth signal 26, derivatives or permutations of the pleth signal 26, and combinations thereof. Fiducial points may include, but are not limited, to the tip of each peak 70, the bottom of the trough 72, the dicrotic notch 74, and other regularly observed turning points such as the point of maximum slope, the point of maximum curvature, a point with zero slope, the pulse mean crossing, and/or a point of zero crossing in the pleth and derivatives thereof.

A fiducial pulse period may be defined as the time between the same fiducial point on two consecutive waves of a pleth signal 26. The example illustrated in FIG. 3 shows that the first fiducial pulse period 82 is the time between the first set of points 80A and 80B, the second fiducial pulse period 86 is the time between the second set of points 84A and 84B, and the third fiducial pulse period 90 is the time between the third set of points 88A and 88B. Fiducial points and fiducial pulse periods for each fiducial point set may be recorded in a memory device of the system including, but not limited to, the nonvolatile memory 60, RAM 42, or ROM 62 (FIG. 2).

The number of fiducial points identified for each wave may vary depending on the regularity of the patient's pulse rate, the quality of the pleth signal 26, the desired level of accuracy in estimating the patient's pulse rate, the desired speed of estimating the patient's pulse rate, and whether an energy saving option has been selected, among other factors. Because each fiducial point is located on a single wave, the number of possible fiducial points is only limited by the sample time and the ability of the system to repeatedly identify the same point on consecutive waves of the waveform. For example, many fiducial points may easily be identified on a pleth signal 26 with little noise. However, noise in a pleth signal 26 may render some fiducial points, such as the dicrotic notch, trough, and peaks, difficult to accurately identify. In some embodiments, more fiducial points may enable a better estimation of the patient's pulse rate or other physiological parameters. In some situations, many fiducial points may be identified to generate many fiducial periods within a short period of time, so that an estimated pulse rate may be determined more quickly. As the pleth signal 26 changes, the number of identified fiducial points may change due to the same factors described above.

Recording each fiducial point in memory may include recording a fiducial point identifier, the time a fiducial point was recorded, the amplitude of a recorded point, and/or the direction or derivative (e.g., increasing or decreasing) of the signal at a recorded fiducial point. In an embodiment, every fiducial point identified may be recorded in memory and be used to estimate the patient's pulse rate. More recorded fiducial periods may improve the estimation of the patient's pulse rate, particularly if the fiducial periods are relatively consistent for each fiducial point set. The sample size is only limited by the number of points that may be stored in memory. Of course, the sample size may be limited to sets of fiducial points within a recent period of time, such as the last sixty seconds. In other embodiments, the sample size may be limited to sets of fiducial points since the system settings were modified, such as when a signal filter is changed. The sample size may also be limited to relatively consistent fiducial periods.

The recorded fiducial pulse periods may fall within a range of values for each sample. The fiducial pulse periods may vary within any sample due to factors including measurement error, signal noise, and pulse irregularities. Measurement error may be the discrepancy between multiple measurements of the same parameter. Measurement error may be reduced through calibration and consistent measurement procedures, but may not be eliminated entirely. Signal noise may cause shifts in the pleth signal 26 that causes misidentification of a fiducial point along a wave. Also, a patient's pulse may not be regular at all times. Thus, fiducial pulse periods may differ from one set to another. Of course, from a statistics perspective, variations in multiple measurements of the same parameter may always exist, and these variations may provide additional information about the measurements and help contribute to an estimated accuracy of the measurements.

Figure 4:
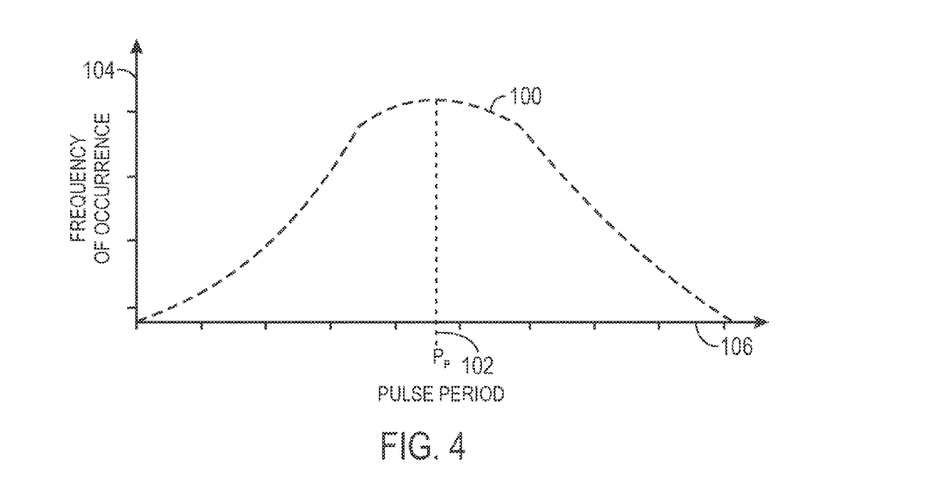
FIG. 4 is a chart depicting a Gaussian distribution curve, in accordance with aspects of the present disclosure.

Recorded fiducial pulse periods from all sets of fiducial points may be shown on a distribution curve. FIG. 4 shows a distribution curve 100 for a theoretical fiducial point or set of fiducial points. For a known sample size, the distribution curve 100 charts the frequency of occurrence 104 of all pulse period times 106 occurring over the sample. The peak 102 of the distribution curve 100 may be taken as the most probable fiducial pulse period over the sample size.

Figure 5:
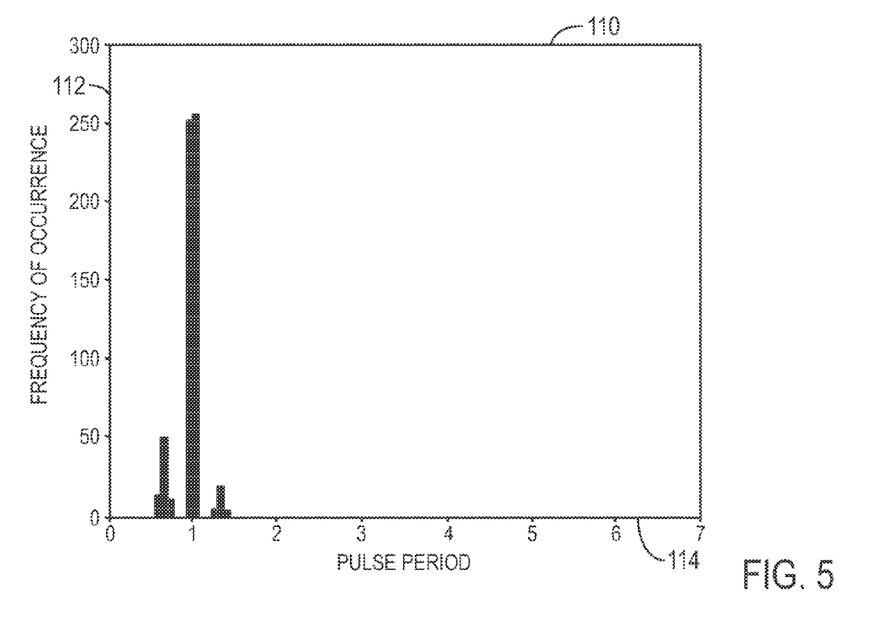
FIG. 5 is a histogram depicting the prevalence of particular pulse periods for a sample, in accordance with aspects of the present disclosure.

Histograms may be used to show the actual distribution of a data set. FIG. 5 illustrates a histogram 110 of fiducial pulse periods taken from a sample pleth signal such as 26 (FIG. 3). FIG. 5 charts the frequency of occurrence 112 of fiducial pulse period ranges 114 over a known sample size. This shows the actual fiducial periods measured from multiple fiducial points on a sample of pulses. To form the histogram 110, all sampled fiducial pulse periods are sorted into bins associated with a particular range of pulse periods. The histogram 110 plots the frequency of sampled fiducial periods within each bin with a bar, resulting in a chart of the histogram bars. A histogram 110 may only illustrate the frequency of pulse period ranges that occurred in the past. Using a histogram, one may only estimate a range of the most likely pulse period for a patient. For example, the most likely pulse period may be between 0.99 and 1.01 seconds in the sampled fiducial periods of the histogram 110.

Figure 6:
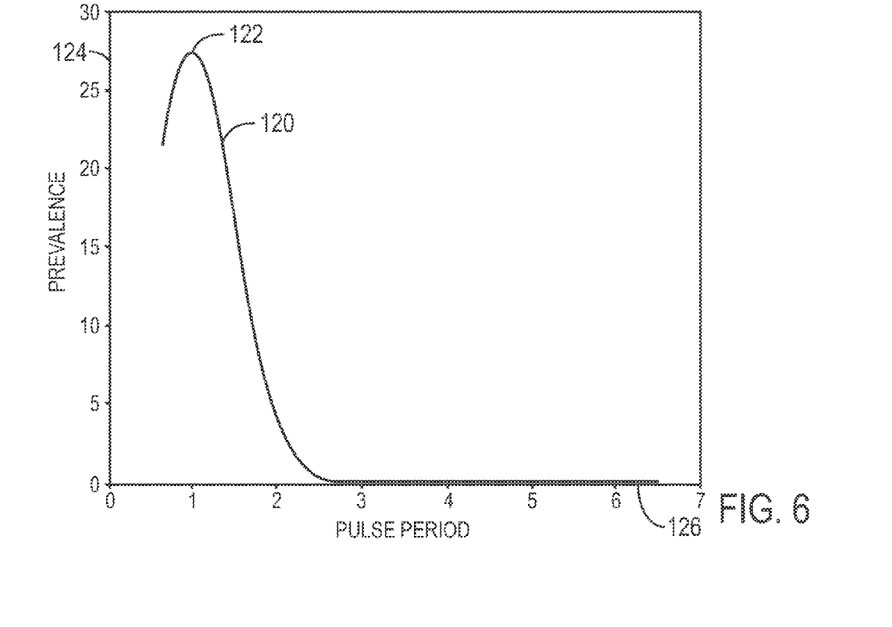
FIG. 6 is a chart depicting a smoothed Gaussian kernel distribution of pulse periods from the sample of FIG. 5, in accordance with aspects of the present disclosure.

A specific pulse period, rather than a range of pulse periods, may be estimated from the same sample used in FIG. 5 by using Gaussian kernel smoothing as shown in FIG. 6. The peak 122 of the smoothed curve 120 indicates the most probable pulse period to occur utilizing all the recorded fiducial pulse periods. The smoothed Gaussian kernel distribution curve 120 charts the prevalence of a pulse period 124 of a pulse period occurring for all pulse period times 126. As described below, all recorded periods are converted into Gaussian kernel functions and summed to create this smoothed Gaussian kernel distribution curve 120.

Figure 7:
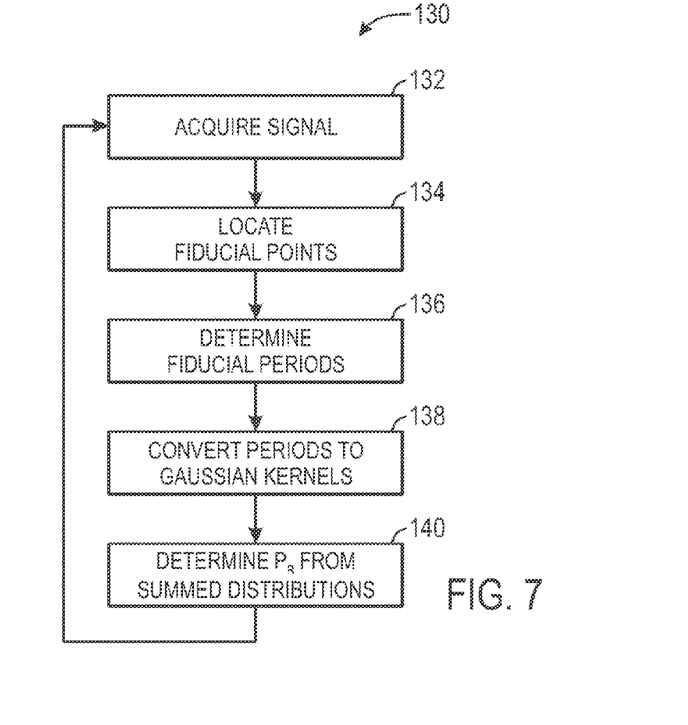
FIG. 7 is a flowchart depicting a method for operating a pulse oximeter to determine a pulse rate, in accordance with aspects of the present disclosure.

The Gaussian kernel smoothing method 130 illustrated in FIG. 7 may be used to generate the Gaussian kernel smoothed curve 120 to determine a patient's most probable pulse rate. The Gaussian kernel smoothing method 130 does not give extra weight to any particular pulse periods. The Gaussian kernel smoothing method 130 may be executed in software, for example, by the processor 38 (FIG. 2), by an external computer system (not illustrated) that may be coupled to the monitor 14, or, alternatively, executed in hardware/firmware of an application-specific integrated circuit (ASIC) (not shown) of the monitor 14.

In this embodiment, the Gaussian kernel smoothing method 130 begins by acquiring (block 132) a signal. Fiducial points are then located (block 134) on each wave of the acquired pleth signal as illustrated in FIG. 3. In some embodiments, multiple fiducial points are located on each wave of the acquired pleth signal, resulting in multiple sets of fiducial points, and thus multiple fiducial periods, for each consecutive pleth wave. In other embodiments, only one fiducial point is located on each pleth wave, resulting in only one set of fiducial points, and thus one fiducial period, for each consecutive pleth wave. The fiducial points are recorded in memory as described above.

The located sets of fiducial points are utilized to determine (block 136) fiducial pulse periods for each set. The fiducial pulse period may be generally the time between two fiducial points of the same set. Each determined fiducial pulse period represents the measured pulse rate for each respective pleth wave. All determined fiducial pulse periods are also recorded in memory as described above.

After fiducial pulse periods for each fiducial point set are determined (block 136), each fiducial pulse period is converted (block 138) into a Gaussian kernel function. A Gaussian kernel is a Gaussian distribution curve with a set shape and distribution. A Gaussian, distribution curve is one such that the median, mean, and mode are the same value. Each Gaussian kernel is centered on its respective recorded fiducial pulse period. This conversion may be illustrated in FIG. 8 for a theoretical sample size. The recorded fiducial periods 127 are indicated on the x-axis 126 plotting time. The probability 128 of each recorded pulse period is indicated on the y-axis. An identical Gaussian kernel distribution curve 121 is centered over each recorded fiducial period 127. Furthermore, each Gaussian kernel has the same standard deviation a, leading each Gaussian kernel curve 121 to have the same shape and distribution. Each Gaussian kernel function has a value for all period times along the x-axis 126. Thus, the Gaussian kernel distribution curve 121 for each recorded fiducial period 127 may overlap with the Gaussian kernel distribution curves 121 of other recorded fiducial periods 127.

Figure 8:
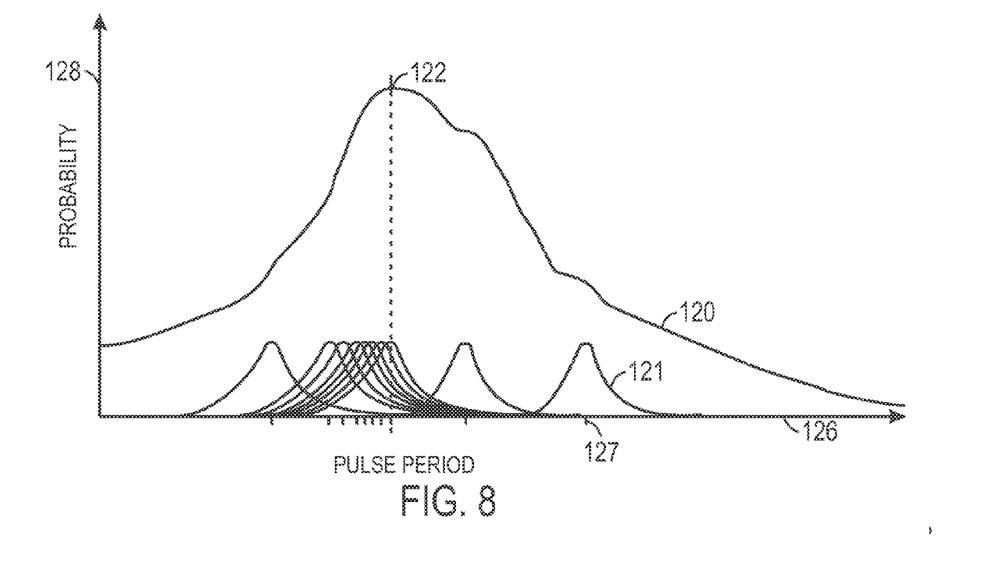
FIG. 8 is a chart depicting a sample of fiducial periods converted into Gaussian kernel functions and summed according to the method shown in FIG. 7, in accordance with aspects of the present disclosure.

The Gaussian kernel distributions for all recorded fiducial pulse periods over the sample time are summed (block 140) together. This summation involves summing together the distribution of each Gaussian kernel over all pulse period times. For example, the Gaussian kernel smoothed distribution curve 120 of FIG. 8 is the summation of each Gaussian kernel distribution curve 121 for all pulse period times. The sum of all Gaussian kernel distributions for each pulse period relates to the probability of that pulse period being the patient's true pulse period. The resulting Gaussian kernel smoothed distribution curve 120 relates to a probability distribution of pulse periods based on all the recorded fiducial pulse periods. A patient's pulse rate may then be derived from the Gaussian kernel smoothed distribution curve 120 as the pulse period corresponding to the greatest probability of occurrence. Referring to FIG. 8, the patient's pulse period corresponds to the peak 122 of the Gaussian kernel smoothed distribution curve 120.

A patient's pulse rate ($P_R$) in pulses per minute can be derived from the pulse period ($P_P$) in seconds per pulse as follows:

$$P_R = (1/P_P) \times 60 \qquad (1)$$

As derived by the Gaussian kernel smoothing method 130, this pulse rate may or may not correspond to any actual recorded fiducial pulse period. Furthermore, this method 130 utilizes all recorded data without explicitly weighting any recorded data.

The value of the standard deviation utilized for the Gaussian kernel distributions may affect the width of each distribution curve 121. The standard deviation thus affects the summation of the Gaussian kernel distributions. In some embodiments, the standard deviation, may be derived dynamically, for example, from the recorded fiducial pulse periods. In other embodiments, the standard deviation may be predefined. In an embodiment, the standard deviation is set at about 0.5. The standard deviation used for each Gaussian kernel influences the amount of smoothing. Over-smoothing may obscure the underlying structure of the fiducial period distribution whereas under-smoothing may result in the preservation of data artifacts such as noise.

As discussed above, Gaussian kernel functions may be calculated for all pulse period times, thus Gaussian kernel functions are infinite in width. However, in practice Gaussian kernel functions may be calculated only for physiological possible pulse periods. For example, a pulse period of 0.4 seconds corresponds to a pulse rate of 150 beats per minute, while a pulse period of 1.5 seconds corresponds to a pulse rate of 40 beats per minute as under equation (1). A Gaussian kernel function centered on 0.4 seconds overlaps the Gaussian kernel function centered on 1.5 seconds to at least a small extent regardless of the standard deviation of the Gaussian kernel function utilized. The summation (block 140) of all Gaussian kernel distributions 121 may sum the distribution from each converted fiducial period 127 regardless of its value to generate the Gaussian kernel smoothed curve 120. This enables all recorded data that might be physiologically possible to contribute to the derivation of the patient's pulse rate.

While all recorded fiducial pulse period data may be utilized to derive the Gaussian kernel smoothing curve, in some embodiments only subsets of the recorded data are utilized, such as only data from a particular fiducial point or points, the most recent data, or the recent data only if a clear strong signal is acquired. Once the patient's pulse rate is determined based on the Gaussian kernel smoothing method 130, the processor 38 repeats the above steps starting with receiving (block 132) the pleth signal and locating (block 134) fiducial points.

The Gaussian kernel smoothing method 130 may be utilized for any pleth signal 26. However, signal noise, measurement errors, and anomalous signals may affect the estimation of the patient's pulse rate. To reduce these effects, filters may be applied to the signal, pulse periods, or both. Turning to the filtering method 150 shown in FIG. 9, pulse periods corresponding to extreme and/or unlikely physiological conditions may be removed from utilization to determine the patient's pulse rate. Pulse periods corresponding to extreme and/or unlikely physiological conditions may result from noise or other irregularities in the signal. As discussed above, signal noise may come in many forms from different sources. Such noise may be of any frequency or range of frequencies. In some embodiments, signal indicators of known noise sources may enable the sensor 12 or monitor 14 to identify and remove noise sources.

Figure 9:
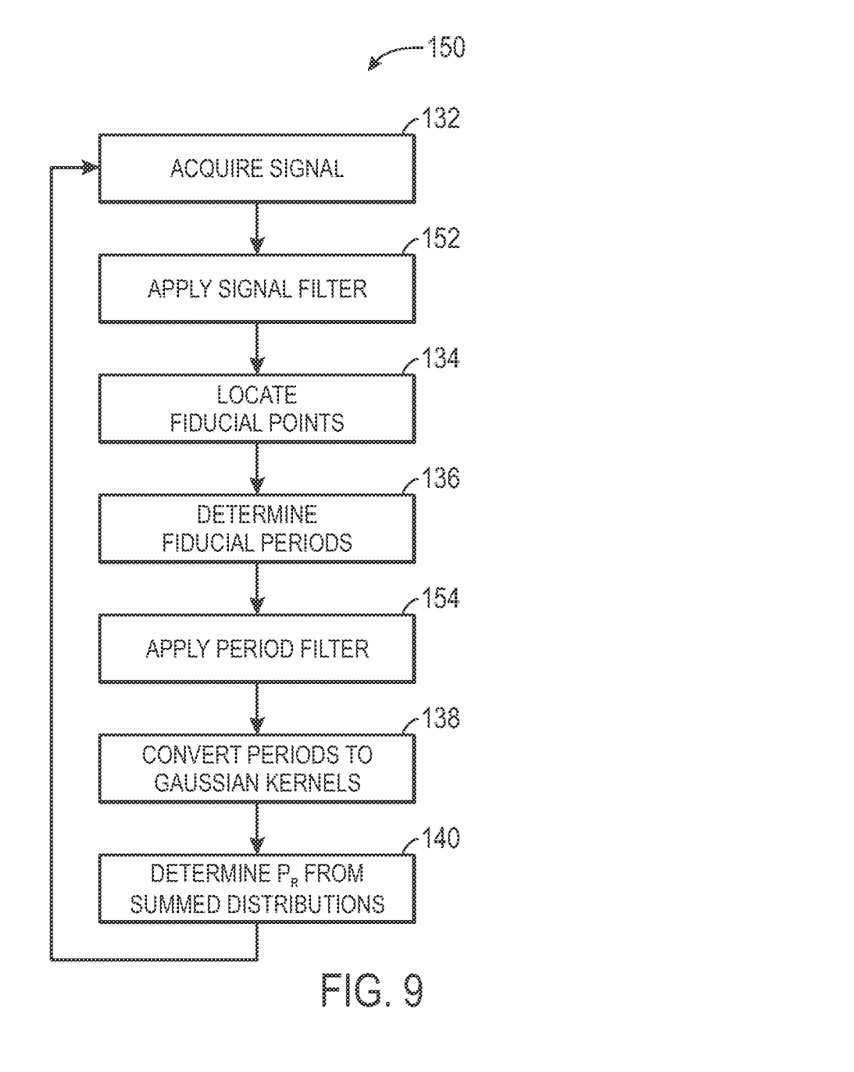
FIG. 9 is a flowchart depicting a method for operating a pulse oximeter to determine a pulse rate with filters, in accordance with aspects of the present disclosure.

In other embodiments, the acquired signal may be filtered (block 152) before fiducial points are located (block 134). Other embodiments may apply (block 154) a filter to the determined fiducial pulse periods. A filter applied to the determined fiducial pulse periods may remove all fiducial pulse periods from memory corresponding to pulse rates outside a known range (e.g., 20-350 pulses per minute). However, other fiducial pulse period filter ranges may be applied. Some fiducial pulse periods may be removed from memory by the filter because that particular fiducial pulse period is an outlier and may skew the pulse rate as determined by the Gaussian kernel smoothing method 130. In some embodiments, a fiducial pulse period may be removed from memory due to a measurement error, noise, or an anomalous signal. In other embodiments, no filter may be applied to recorded fiducial pulse periods. Filters may be applied before fiducial points are located as indicated by block 152, right before fiducial pulse periods are converted to Gaussian kernel functions as indicated by block 154, or at both instances. Of course, in other embodiments, the signal filter 152 and the period filter 154 may be omitted.

The accuracy of the estimated pulse rate from Gaussian kernel smoothing method 130 depends on the quality of the underlying data, namely the fiducial points. Changing the number of the fiducial points utilized may affect the accuracy of the estimated pulse rate. However, each fiducial point is unique and may not have the same impact on the accuracy of the estimated pulse rate. Some fiducial points may be more reliable than other fiducial points. Furthermore, some fiducial points may be easier to identify on each wave. These aspects and others may be different for each fiducial point. Fiducial points may be ranked according to such aspects such that a number of high ranked fiducial points identified on the pleth signal 26 may provide a more accurate pulse rate estimate than the same number of lower ranked fiducial points.

Fiducial point ranking may be based on the reliability, consistency, location, and/or quality of each fiducial point, among other factors. The reliability factor of a fiducial point may be a measure of how closely the fiducial point correlates to an aspect of the patient's physiology. The consistency factor may be a measure of the regularity of pulse periods based on the fiducial point. The location factor may be a measure of the ease of identification of the fiducial point from a pleth signal, such as the amount of processing required to locate the fiducial point. The quality factor may be a measure of the lack of noise typically found at a fiducial point. Other factors may also be used to rank fiducial points stored in memory. In some embodiments, fiducial points may have multiple rankings, with each ranking taking into account factors considered individually or together in various combinations. Alternatively, fiducial points may only have a single ranking taking all factors into account. In certain embodiments, the ranking of fiducial points is predetermined and static. In certain other embodiments, fiducial points may be ranked dynamically with the ranking of each point based on its effect on the Gaussian kernel distribution.

Additionally, the number, N, of ranked fiducial points loaded from memory may change according to various conditions. N may represent the number of fiducial points located on consecutive signal waves. As an example, engaging an energy saving option may change N to load and process fewer fiducial points to consume less energy. As another example, N may be decreased if the patient's pulse rate is very regular because the pulse rate determinations are accurate. However, if the patient's pulse rate is very irregular, additional fiducial points may be desirable to increase resolution or provide additional physiological information available due to many fiducial points providing reliable and accurate information. In some embodiments, N may be decreased if a signal is noisy or the smoothed Gaussian distribution of the pulse rate is wide. In other embodiments, N may be increased to reduce the effect of noise on the pulse rate determination. Also, N may change over time for other reasons. For example, N with a large initial value may provide a faster accurate determination of a patient's pulse rate than if N had a small initial value.

Figure 10:
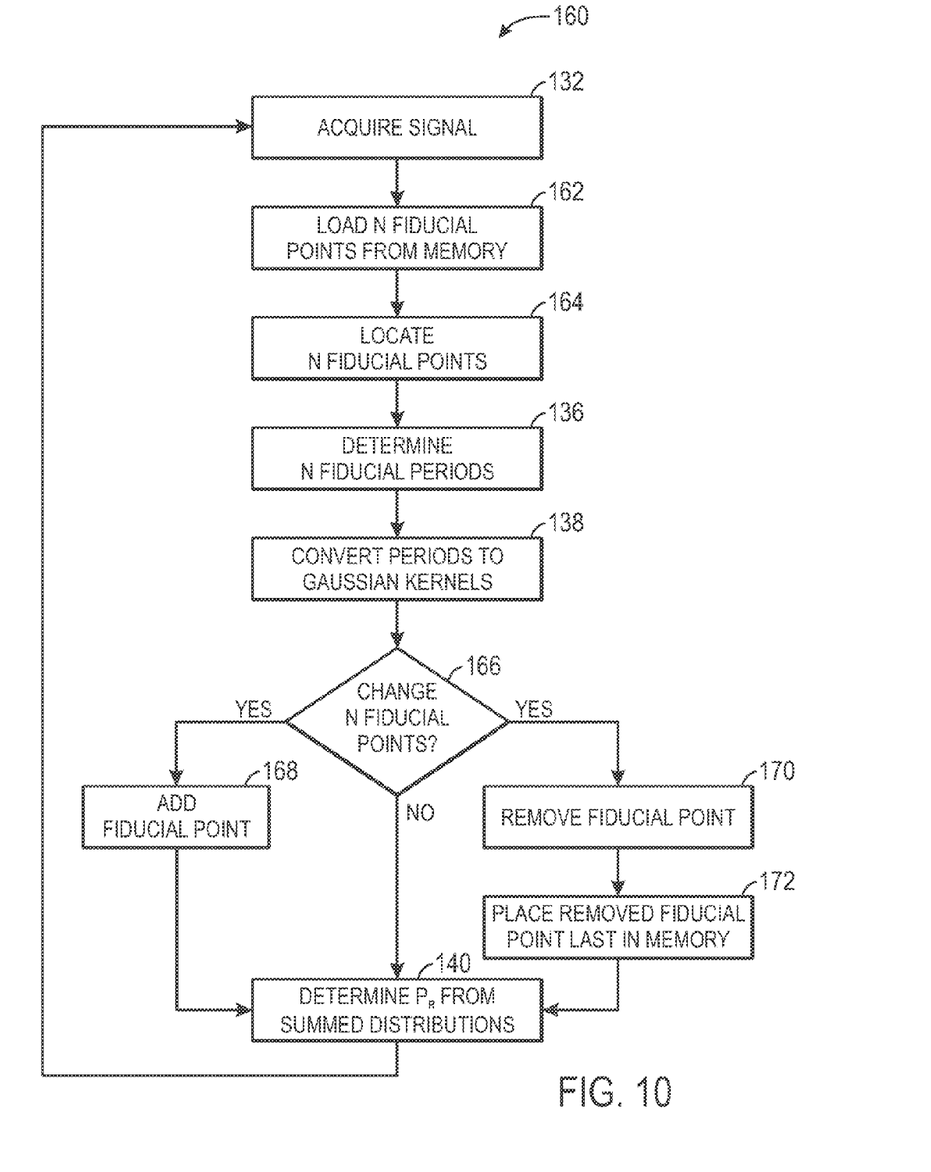
FIG. 10 is a flowchart depicting a method for operating a pulse oximeter to determine a pulse rate after loading ranked fiducial points from a memory device, in accordance with aspects of the present disclosure.

The N fiducial points loaded from memory may have a static or dynamic ranking. The ranking method 160 derives a Gaussian kernel smoothing curve based on N ranked fiducial points loaded from memory as shown in FIG. 10. In this embodiment, the ranking method 160 begins by acquiring (block 132) a signal. Then N fiducial points are loaded (block 162) from memory. As described above, the memory may be any memory device of the system including, but not limited to, the nonvolatile memory 60, RAM 42, or ROM 62 (FIG. 2). Further, the loaded fiducial points are selected from memory based on their rank. Fiducial points are loaded in rank order, with highly ranked fiducial points loaded first. Thus, if N is set to three, the highest ranking fiducial point is loaded first, followed by the second highest ranked fiducial point, then the third highest fiducial point.

Once N ranked fiducial points are loaded (block 162) from memory, N ranked fiducial point sets are located (block 164) on the pleth signal. After the ranked fiducial point sets are located, the fiducial pulse periods are determined (block 136) and recorded in memory. Then each recorded fiducial pulse period is converted (block 138) into a Gaussian kernel function. As described above with FIG. 7, each Gaussian kernel is centered on its respective recorded fiducial pulse period.

In this embodiment, the processor 38 or another device executing the ranking method 160 determines whether to increase, decrease, or maintain N fiducial points utilized in the Gaussian kernel smoothing method. The processor 38 may determine (step 166) an increase or decrease of N fiducial points loaded from memory based on several conditions, including, but not limited to, user input, number of sampled pleth waves, iterations of ranking method 160 since the last change to the N, and properties of the resulting Gaussian kernel smoothing curve. The end user may also specify the value of N to be utilized through hardware or software. For example, the end user may make changes through the control inputs 64 or the network interface card 66 of the monitor 14. N may be changed whether the fiducial points have a static or dynamic ranking.

The processor 38 may also change N based on the standard deviation of the Gaussian kernel smoothing curve. In some embodiments, a Gaussian kernel smoothing curve with a small standard deviation may indicate a strong signal with little noise and a small range of measured pulse periods. The processor 38 may add (block 168) more fiducial points to the pulse rate determination for many reasons, including improving the accuracy of the determined pulse rate or determining additional physiological parameters. In some embodiments, adding fiducial points may increase the accuracy of the determined pulse rate without a significant effect on the standard deviation of the Gaussian kernel smoothing curve 120. A Gaussian kernel smoothing curve with a narrow distribution may be able to utilize additional less highly ranked fiducial points for a more accurate determination of the patient's pulse rate. In other embodiments, a small standard deviation may indicate that less fiducial points may be utilized (N may be lowered) yet substantially the same determined pulse rate may be determined while consuming less energy.

Other aspects of the same embodiments may decrease (block 170) N. A noisy pleth signal may result in a large standard deviation of the Gaussian kernel smoothing curve. The highest ranked points may provide a consistent pulse period and be relatively easy to locate despite the noise, whereas low ranked points if utilized may provide irregular pulse periods and increase the standard deviation of the Gaussian kernel smoothing curve. Removing the fiducial pulse periods of the low ranking fiducial points from utilization in the Gaussian kernel smoothing curve may decrease the standard deviation of the Gaussian kernel smoothing curve. A decrease in the standard deviation narrows the Gaussian kernel smoothing curve, thus improving the accuracy of the patient's pulse rate determination.

For embodiments with a dynamic ranking, the rank of a fiducial point may be changed based on its effect on the Gaussian kernel smoothing curve. When the ranking is dynamic, the ranking is an alterable property of each fiducial point. For example, a fiducial point with an initial high ranking may be given a low ranking if fiducial pulse periods derived from that fiducial point are very irregular. In embodiments with multiple rankings for each fiducial point, rankings may be dependent or independent of other rankings. For example, a fiducial point with high consistency, quality and overall rankings may have its quality ranking lowered due to noise at that fiducial point over a sample size. Lowering the quality ranking may also lower the overall ranking without affecting the consistency ranking.

In some dynamic ranked embodiments, when N is decreased, thus removing the $N^{th}$ ranked fiducial point from utilization, the rank of the $N^{th}$ point may be changed. For example, fiducial points ranked poorly for consistency may be removed (block 170) when only a few fiducial points are to be utilized for any reason. If the processor 38 decreases N as indicated by block 170, the ranking of the removed fiducial points will be lowered according to the reason it was removed. For example, the overall ranking of each fiducial point, the rank according to a particular factor, or both ranks may be lowered when a fiducial point is removed from utilization. In some embodiments as indicated by block 172, when the ranking of a fiducial point is lowered, its ranking is decreased from an initial ranking to the lowest ranking and all intervening fiducial points are shifted higher in rank by one position. For example, if a certain fiducial point ranked 10 out of 25 fiducial points in memory is removed, that certain fiducial point will be ranked 25 and the 15 fiducial points previously ranked 11-25 will be moved up to have rankings 10 to 24. Thus, in embodiments with this revolving ranking system, a fiducial point removed from utilization will only be reconsidered after all other fiducial points have been utilized.

In some situations, the processor may maintain the value of N for a minimum amount of time, iterations, or pulse periods before permitting a change. The processor 38 may also maintain N if no more fiducial points may be loaded from memory. Likewise, the processor 38 may not remove fiducial points from utilization if only one point is currently being utilized.

In some embodiments, all fiducial points are located on the signal as it is acquired and all fiducial pulse periods are recorded in memory at all times. However, the Gaussian kernel smoothing curve only takes into account the fiducial periods from the highest ranked N fiducial points. If the processor 38 increases (block 168) N, then all the fiducial pulse periods previously recorded for the additional point(s) may be utilized immediately. Thus, the Gaussian kernel smoothing curve is based on all fiducial pulse periods recorded from N fiducial points, not all recorded data. In this embodiment, the processor 38 may determine N based on the value of N that provides the smallest standard deviation of the Gaussian kernel smoothing curve.

After any changes with respect to the value of N are made, the Gaussian kernel distributions for all recorded fiducial pulse periods over the sample size are summed (block 140) together. The resulting summation represents a probability distribution of pulse periods based on all the recorded fiducial pulse periods utilized in this iteration of ranking method 160. As described above, a patient's pulse rate may then be derived from the summation. While this determined pulse rate may or may not correspond to any particular actual recorded fiducial pulse period, this Gaussian kernel smoothing summation utilizes all recorded data from N fiducial points. Once the patient's pulse rate is determined based on the Gaussian kernel smoothing summation, the processor 38 may repeat the above steps starting with acquiring (block 132) the pleth signal and loading (block 162) the highest N ranked fiducial points from memory. Furthermore, the ranking method 160 may incorporate filters at any point as described above with FIG. 9.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Indeed, the disclosed embodiments may not only be applied to measurements of pulse rate, but these techniques may also be utilized for the measurement and/or analysis of other physiological parameters. Furthermore, it may be appreciated by one skilled in the art that while the embodiments described herein include pulse oximeters and pleth signals, the methods described herein may be applied to pleth signals or other signals acquired from another device. Rather, the various embodiments may cover all modifications, equivalents, and alternatives falling within the spirit and scope of the disclosure as defined by the following appended claims.

What is claimed is:

1. A method for determining a physiological parameter from a physiological signal using a processor of an electronic device, comprising:
   identifying at least one fiducial point on consecutive waves of the physiological signal, using the processor;
   wherein the at least one fiducial point comprises a peak of the physiological signal, a trough of the physiological signal, a dicrotic notch of the physiological signal, a point of maximum slope of the physiological signal, a point of maximum curvature of the physiological signal, a pulse mean crossing of the physiological signal, a point of zero crossing in the physiological signal, or a point of zero crossing in a derivative of the physiological signal, or any combination thereof;
   wherein corresponding fiducial points of the consecutive waves form sets of fiducial points;
   determining a fiducial period for each set of fiducial points using the processor;
   converting each of the fiducial periods to a respective Gaussian kernel function using the processor;
   summing the Gaussian kernel functions to create a distribution curve using the processor;
   determining the physiological parameter from the distribution curve using the processor; and
   displaying on a display the determined physiological parameter.

2. The method, as set forth in claim 1, wherein identifying the at least one fiducial point comprises recording data for each fiducial point, wherein data comprises a fiducial point identifier, a time of the fiducial point, an amplitude of the fiducial point, a derivative of the physiological signal at the fiducial point, or any combination thereof.

3. The method, as set forth in claim 1, wherein identifying the at least one fiducial point comprises identifying fiducial points based on a ranking of the fiducial points.

4. The method, as set forth in claim 3, wherein the ranking of the fiducial points is based on a reliability factor of each fiducial point, a consistency factor of each fiducial point, a location factor of each fiducial point, or a quality factor of each fiducial point, or any combination thereof.

5. The method, as set forth in claim 1, wherein the steps of claim 1 are carried out for at least one prior iteration; wherein identifying the at least one fiducial point comprises identifying fiducial points based on a ranking of the fiducial points; and wherein the ranking of each fiducial point is dynamic and based on an effect the respective Gaussian kernel function has on the distribution curve of the at least one prior iteration.

6. The method, as set forth in claim 1, wherein identifying the at least one fiducial point comprises identifying the at least one fiducial point based on a user input number.

7. The method, as set forth in claim 1, wherein determining the physiological parameter from the distribution curve comprises determining the peak of the distribution curve.

8. The method, as set forth in claim 1, further comprising filtering the fiducial periods to remove fiducial periods corresponding to a heart rate outside the range of about 20-350 beats per minute (BPM).

9. The method, as set forth in claim 1, further comprising filtering the physiological signal to remove a non-physiological signal component.

10. The method, as set forth in claim 1, wherein a standard deviation of each Gaussian kernel function is about 0.5.

11. A monitor comprising:
a processor configured to:
identify at least one fiducial point on consecutive waves of a physiological signal;
wherein the at least one fiducial point comprises a peak of the physiological signal, a trough of the physiological signal, a dicrotic notch of the physiological signal, a point of maximum slope of the physiological signal, a point of maximum curvature of the physiological signal, a pulse mean crossing of the physiological signal, a point of zero crossing in the physiological signal, or a point of zero crossing in a derivative of the physiological signal, or any combination thereof;
determine a fiducial period between the at least one fiducial point for each consecutive wave;
convert each of the fiducial periods to a respective Gaussian kernel function;
sum the Gaussian kernel functions to create a distribution curve;
determine a physiological parameter from the distribution curve; and
a memory configured to store data associated with each identified fiducial points.

12. The monitor, as set forth in claim 11, wherein the processor is configured to identify at least one fiducial point based on a ranking of the fiducial points, wherein the ranking of the fiducial points is based on a reliability factor of each fiducial point, a consistency factor of each fiducial point, a location factor of each fiducial point, or a quality factor of each fiducial point, or any combination thereof.

13. The monitor, as set forth in claim 12, wherein the processor is configured to determine a physiological parameter from the distribution curve created by the sum of a subset of Gaussian kernel functions.

14. The monitor, as set forth in claim 11, wherein the data stored in memory comprises a fiducial point identifier for each fiducial point, a time the fiducial point was identified, an amplitude of the identified fiducial point, or a derivative of the physiological signal at the identified fiducial point, or any combination thereof.

15. The method, as set forth in claim 1, wherein the at least one fiducial point is identified on consecutive waves of the physiological signal in the time domain.

16. The method, as set forth in claim 1, wherein the at least one fiducial point is identified from a derivative of the physiological signal.

17. The method, as set forth in claim 1, wherein identifying at least one fiducial point comprises identifying a plurality of different fiducial points on consecutive waves of the physiological signal.

18. The method, as set forth in claim 1, wherein the physiological signal is a plethysmographic signal.

* * * * *